US00PP17083P2

(12) United States Plant Patent
Zary

(10) Patent No.: US PP17,083 P2
(45) Date of Patent: Sep. 5, 2006

(54) FLORIBUNDA ROSE PLANT NAMED 'JACTHAIN'

(50) Latin Name: *Rosa hybrida*
Varietal Denomination: JACthain

(75) Inventor: Keith W. Zary, Agoura Hills, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 11/139,317

(22) Filed: May 27, 2005

(51) Int. Cl.
*A01H 5/00* (2006.01)

(52) U.S. Cl. ..... Plt./141

(58) Field of Classification Search ..... Plt./141, Plt./146

See application file for complete search history.

*Primary Examiner*—Kent Bell
*Assistant Examiner*—June Hwu
(74) *Attorney, Agent, or Firm*—Klarquist Sparkman LLP

(57) ABSTRACT

Floribunda rose plant having strong, spicy fragrance; novel, copper and pink flower color; attractive, hybrid tea-shaped blooms; ease of propagation from softwood cuttings; flowers presented in clusters; and resistant to rust and powdery mildew.

1 Drawing Sheet

Genus and species: *Rosa hybrida.*
Variety denomination: 'JACthain'.

ORIGIN OF THE INVENTION

The present invention relates to a new and distinct variety of a floribunda rose plant named 'JACthain' which was originated by me by crossing the variety 'MACivy' (U.S. Plant Pat. No. 8,362), with an unnamed pink floribunda seedling (not patented) ('JACship' (U.S. Plant Pat. No. 7,948)×'JACdew' (U.S. Plant Pat. No. 5,122)).

BACKGROUND OF THE INVENTION

The primary objective of this breeding was to produce a new rose variety having the fragrance, flower color and flower form of the female parent combined with the healthy, dark green foliage, compact plant and excellent clustering ability of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Strong, spicy fragrance.
2. Novel, copper and pink flower color.
3. Attractive, hybrid tea-shaped blooms.
4. Ease of propagation from softwood cuttings.
5. Flowers presented in clusters.
6. Resistant to rust and powdery mildew.

Asexual reproduction of this new variety by cuttings, as performed at Wasco, Calif., shows that the foregoing and all other characteristics and distinctions come true to form and are established and transmitted through succeeding propagations.

Comparison with Parents

The flowers and foliage of 'JACthain' are larger than those of the female parent and the plant is more spreading in shape. Compared to the male parent, flowers of 'JACthain' are different in color and fragrance, and the plants are larger, i.e., taller.

Comparison with Similar Variety

The closest variety to 'JACthain' is 'MACivy'. The flowers and foliage of 'JACthain' are larger than from those of 'MACivy' and the plant is more spreading in shape.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'MACivy' (U.S. Plant Pat. No. 8,362).

*Pollen parent.*—Unnamed pink floribunda seedling ('JACship' (U.S. Plant Pat. No. 7,948)×'JACdew' (U.S. Plant Pat. No. 5,122)) (not patented).

FLOWER

Observations made from January 2003 to August 2004 from plants commencing at three years of age grown in a garden environment at Somis, Calif.

Blooming habit: Continuous.

Bud:

*Size.*—About 3.5–4 cm long and 2.5–3 cm in diameter when the petals start to unfurl.

*Form.*—The bud form is pointed ovoid.

*Color.*—When sepals first divide, bud color is Red Group 42B with occasional striation of Yellow-Orange Group 23C. When half blown, the upper sides of the petals are Orange-Red Group 32C with Yellow Group 13A at base and the lower sides of the petals are Red Group 47C with Yellow Group 13A at base.

*Sepals.*—Color: Upper surface: Green Group 143D occasionally with major areas of Greyed-Red Group 181A. Lower surface: Greyed-Red Group 181A with fringes of Green Group 143C. Length: 38–40 mm. Width: 10–15 mm. Shape: Subulate. Surface texture: Upper: Canescent. Lower: Glandular. There are three lightly appendaged sepals. There are two unappendaged sepals with hairy edges.

*Receptacle.*—Color: Green Group 143C. Shape: Pear. Size: Medium, about 5 mm long×7 mm wide. Surface: Smooth.

*Peduncle.*—Length: Medium, averaging about 6–8 cm. Surface: Glandular. Color: When Young: Greyed-Red Group 181A. When Mature: Green Group 143C. Strength: Stiff, erect.

Bloom:

*Size.*—Medium. Average open diameter is about 8–10 cm.

*Borne.*—In pyramidal clusters of 3–7 blooms.

*Stems.*—Strength: Normal. Average length is about 25–30 cm with a diameter of 6–10 mm.

*Form.*—When first open: High centered. Permanence: All petals curl slightly.

*Petalage.*—Number of petals under normal conditions: 25.

*Color.*—The upper sides of the inner petals are Orange Group 29A; those of the outer petals Red Group 47C. The reverse sides of the inner petals are Red Group 47D; those of the outer petals Red Group 51A. The base of each petal has a Yellow Group 13A color spot. The major color on the upper sides of the inner petals is Orange Group 29A; the outer petals Red Group 47C.

*Variegations.*—Petals occasionally have apex of Red Group 38A.

*Discoloration.*—The general tonality at the end of the first day: Orange Group 29A. At the end of the third day: Orange Group 29A (inner petals); Red Group 47C (outer petals). Further aging: Becomes increasingly Red Group 47C.

*Fragrance.*—Strong, spicy.

Petals:

*Texture.*—Thick.

*Shape.*—Obcordate.

*Surface.*—Smooth.

*Margin.*—Entire. Apex Shape: Obcordate. Base Shape: Cuneate.

*Form.*—Tips slightly recurved.

*Arrangement.*—Imbricated.

*Petaloids.*—Number: 3 to 5. Color: Orange Group 29A with Yellow Group 13A at base and Red Group 38A at apex.

*Persistence.*—Petals drop off cleanly before drying.

*Lastingness.*—On the plant: Long (about 7 days). As a cut flower: Long (about 8–9 days).

Reproductive parts:

*Stamens.*—Number: 70–80. Length: 9–10 mm. Anthers: Length: 3–4 mm. Color: Yellow-Orange Group 16C. Arrangement: Regular around styles. Filaments: Color: Yellow Group 9C. Length: 5–6 mm. Pollen: Color: Orange Group 24D.

*Pistils.*—Number: 50–60. Length: 5–6 mm. Styles: Color: Green-Yellow Group 1D. Length: 4–5 mm. Stigmas: Color: Yellow Group 8B. Length: 1 mm.

*Hips.*—None observed.

PLANT

*Form.*—Bush.

*Growth.*—Vigorous, upright, branching.

*Age at maturity.*—Two years.

*Mature plant.*—Height: 100–120 cm. Width: 80–100 cm.

*Rootstock.*—Own root.

Foliage: Number of leaflets on normal mid-stem leaves: 5 or 7.

*Size.*—Large. About 14 cm long×10 cm wide.

*Quantity.*—Abundant.

*Color.*—New foliage: Upper side: Greyed-Red Group 178A. Lower side: Greyed-Red Group 178A. Old foliage: Upper side: Green Group 139A. Lower side: Green Group 139B.

Leaflets:

*Size.*—About 50 mm long×40 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Yellow-Green Group 146C.

*Petiole rachis.*—Color: Yellow-Green Group 146C. Underside: Rough.

*Auricles.*—None.

*Stipules.*—Length: 10–12 mm; smooth with glands.

*Disease resistance.*—Resistant to rust and powdery mildew and susceptible to blackspot under normal growing conditions.

*Pest resistance.*—Not observed.

*Vein color.*—Green Group 139B.

*Venation pattern.*—Reticulate.

Wood:

*New wood.*—Color: Greyed-Red Group 178A. Bark: Smooth.

*Old wood.*—Color: Green Group 137A. Bark: Smooth.

Prickles:

*Quantity.*—On main canes from base: 12 per 15 cm of stem. On laterals from main canes: 7–9 per 15 cm of stem.

*Form.*—Hooked slightly downward.

*Length.*—8–10 mm.

*Color when young.*—Greyed-Purple Group 184B.

*Color when mature.*—Greyed-Orange Group 166D.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its strong, spicy fragrance; novel, copper and pink flower color; attractive, hybrid tea-shaped blooms; ease of propagation from softwood cuttings; flowers presented in clusters; and resistance to rust and powdery mildew.

* * * * *

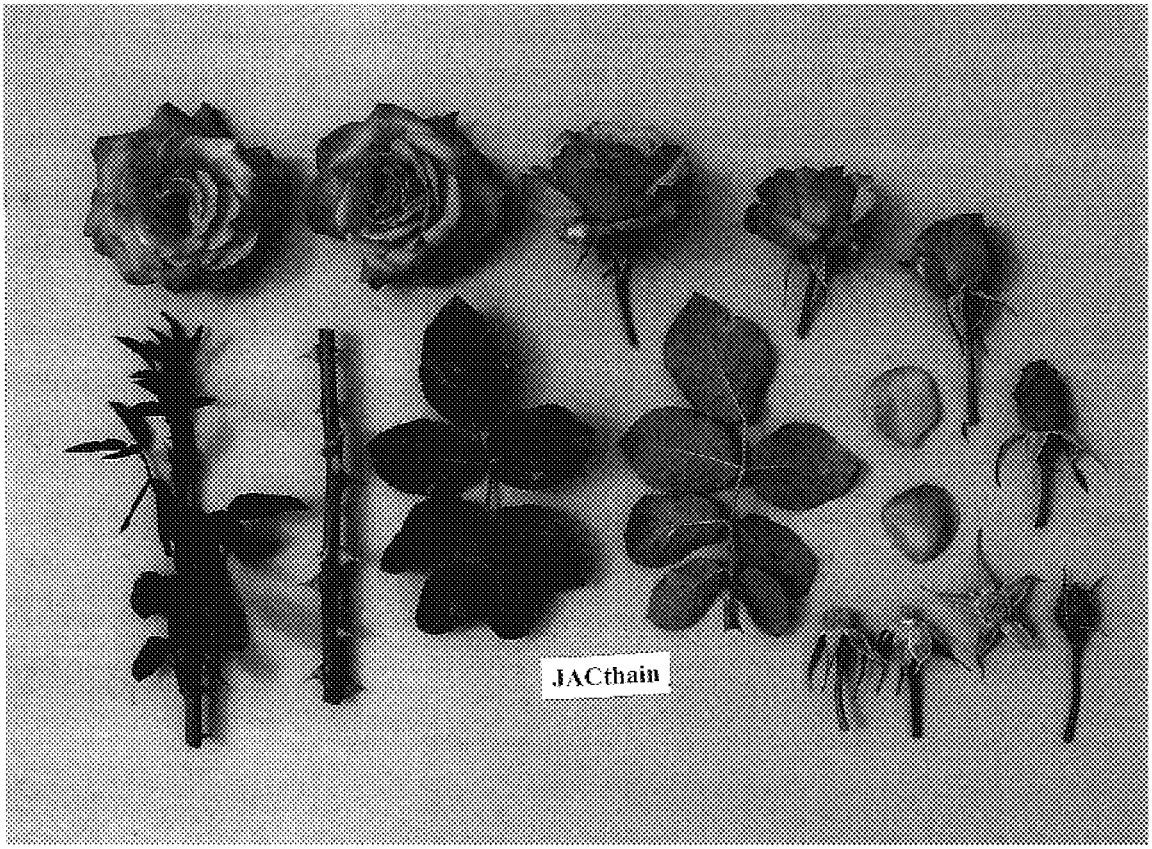
JACthain